United States Patent

Patsch et al.

[11] Patent Number: 5,047,529
[45] Date of Patent: Sep. 10, 1991

[54] PHENYLSULFONES AND CYCLIZATION PRODUCTS THEREOF

[75] Inventors: Manfred Patsch, Wachenheim; Klaus Pandl; Martin Fischer, both of Ludwigshafen, all of Fed. Rep. of Germany

[73] Assignee: BASF Aktiengesellschaft, Ludwigshafen, Fed. Rep. of Germany

[21] Appl. No.: 492,837

[22] Filed: Mar. 13, 1990

[30] Foreign Application Priority Data

Apr. 12, 1989 [DE] Fed. Rep. of Germany ....... 3911975

[51] Int. Cl.$^5$ ............................................. C07D 279/16
[52] U.S. Cl. ........................................................ 544/52
[58] Field of Search ............................................. 544/52

[56] References Cited

FOREIGN PATENT DOCUMENTS 492767 6/1970 Switzerland .
4927660 6/1970 Switzerland .

OTHER PUBLICATIONS

Ber. DT. Chem. GES. vol., 66, pp. 335 to 339, (1933), Rudolf Pummerer, et al.

Primary Examiner—John M. Ford
Attorney, Agent, or Firm—Oblon, Spivak, McClelland, Maier & Neustadt

[57] ABSTRACT

Phenylsulfones of the formula

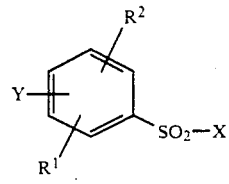

in which
$R$ is hydrogen, halogen, $C_1$-$C_4$-alkyl, nitro, hydroxysulfonyl, carboxyl,
the radical —$NR^3R^4$,
in which $R^3$ and $R^4$ are the same or different and denote hydrogen or $C_1$-$C_4$alkyl, which may or not be substituted,
or the radical $S(O)_nR^5$,
in which n is 0 or 2 and $R^5$ denotes $C_1$-$C_4$-alkyl which may or may not be substituted,
$R^2$ is hydroxy, mercapto or the radical $R^1$,
X is the radical

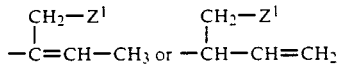

or, with $R^2$ in the ortho-position relative to the group $SO_2$—X,
$R^2$ and X together denote the radial

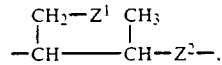

in which
$Z^1$ is hydroxy, chlorine. $C_1$-alkanoyloxy- $C_1$-$C_4$-alkylsulfonyloxy penylsulfonyloxy, o- or p-tolylsulfonyloxy or sulfato and
$Z^2$ is oxygen, sulfur, imino or optionally substituted $C_1$-$C_4$-alkylimino, and
Y denotes amino, $C_1$-$C_4$-alkanoylamino or nitro, and a process for the preparation thereof.

2 Claims, No Drawings

PHENYLSULFONES AND CYCLIZATION PRODUCTS THEREOF

The present invention relates to novel phenylsulfones of formula I

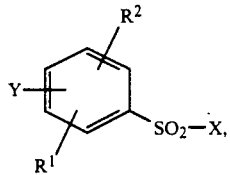

in which
R$^1$ is hydrogen, halogen, C$_1$–C$_4$-alkyl, nitro, hydroxysulfonyl, carboxyl,
the radical —NR$^3$R$^4$,
3 in which R$^3$ and R$^4$ are the same or different and denote hydrogen, C$_1$–C$_4$-alkyl or C$_2$–C$_4$-alkyl substituted by hydroxy. C$_1$–C$_4$-alkanoyloxy, C$_1$–C$_4$-alkoxy hydroxysulfonyl chlorine or bromine.
or the radical S(O)$_n$R$^5$,.
in which n is 0 or 2 and R$^5$ denotes C$_1$–C$_4$-alkyl or C$_2$–C$_4$-alkykyl substituted by hydroxy, chlorine, bromine, C$_1$–C$_4$-alkoxy, hydroxysulfonyl or sulfato,
R$^2$ is hydroxy, mercapto or the radical R$^1$,
X is the radical

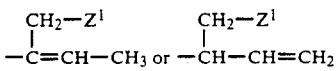

or, with R$^2$ in the orcho-position relative to the group SO$_2$—X,
R$^2$ and X together denote the radical

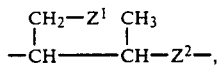

which
Z$^1$ is hydroxy, chlorine, C$_1$–C$_4$-alkanoyloxy. C$_1$–C$_4$-alkylsulfonyloxy, phenylsulfonyloxy, o- or p-tolylsulfonyloxy or sulfato and
Z$^2$ is oxygen, sulfur, imino or C$_1$–C$_4$-alkylimino optionally substituted by hydroxy. 2-hydroxyethylthio or 2-hydroxy ethylsulfonyl, and
Y denotes amino, C$_1$–C$_4$-alkanoylamino or nitro. CH-A-492.766 and CH-A-492,767 describe benzoyl chlorides having, as substituents, butenylsulfonyl radicals containing chlorine in the meta-position and optionally also containing a methyl group.

It is an object of the present invention to provide novel phenylsulfones which may be prepared in a simple manner and can be advantageously used as diazo components or reactive anchors.

Accordingly, we have found the phenylsulfones of formula I defined above.

In formula I, R$^1$, R$^2$, R$^3$, R$^4$ and R$^5$ denote, for example, methyl, ethyl, propyl, isopropyl, butyl, isobutyl or s-butyl.

R$^3$, R$^4$ and R$^5$ may further denote, for example, 2-hydroxyethyl, 2- or 3-hydroxypropyl, 2- or 4-hydroxybutyl, 2-methoxyethyl, 2- or 3-methoxypropyl, 2- or 4-methoxybutyl 2-ethoxyethyl, 2- or 3-ethoxypropyl. 2- or 4-ethoxybutyl, 2-propoxyethyl, 2- or 3-propoxypropyl, 2- or 4-propoxybutyl, 2-isopropylethyl, 2- or 3-isopropoxypropyl, 2- or 4-isopropoxybutyl, 2-butoxyethyl, 2- or 3-butoxypropyl, 2- or 4-butoxybutyl, 2-hydroxysulfonylethyl, 2- or 3-hydroxysulfonylpropyl or 2- or 4-hydroxysulfonylbutyl, 2-chloroethyl, 2- or 3-chloropropyl, 2- or 4-chlorobutyl, 2-bromoethyl, 2- or 3-bromopropyl or 2- or 4-bromobutyl.

R$^5$ may further denote, for example, 2-sulfatoethyl, 2- or 3-sulfatopropyl or 2- or 4-sulfatobutyl.

R$^1$ further denotes, for example, fluorine, chlorine or bromine.

Y denotes, for example, formylamino, acetylamino, propionylamino, butyrylamino or isobutyrylamino.

R$^1$ may also have meanings similar to Z$^1$, for example formyloxy, acetyloxy, propionyloxy, butyryloxy or isobutyryloxy.

Z$^1$ further denotes, for example, methylsulfonyloxy, ethylsulfonyloxy, propylsulfonyloxy, isopropylsulfonyloxy or butylsulfonyloxy.

Z$^2$ denotes, for example, methylimino, ethylimino, propylimino, butylimino, 2-hydroxyethylimino, 2-(2-hydroxyethylthio)ethylimino or 2-(2-hydroxyethylsulfonyl)ethylimino.

Preferred phenylsulfones of formula I are those in which
R$^1$ is hydrogen, halogen or the radical —NR$^3$R$^4$, in which R$^3$ and R$^4$ denote the same or different C$_2$–C$_4$-alkyzl radical substituted by hydroxy and R$^3$ may in addition stand for hydrogen, and
R$^2$ is hydroxy or the radical R$^1$.

Other preferred phenylsulfones of formula I are those in which the radicals R$^2$ and X together form the radical

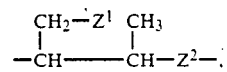

in which Z$^1$ has the meanings stated above and Z$^2$ stands for C$_1$–C$_4$-alkylimino optionally substituted by hydroxy, The phenylsulfones I of the invention may be advantageously obtained by reacting, for example, a sulfinic acid of formula II

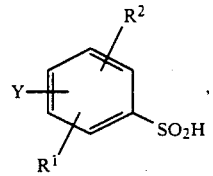

in which Y, R$^1$ and R$^2$ have the meanings stated above, with vinyl oxirane of formula III

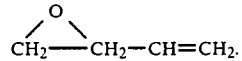

Instead of the sulfinic acid II, a salt thereof may be used, for example an alkali metal salt such as the sodium or potassium salt.

The reaction is conveniently carried out by dissolving the sulfinic acid II in water at a pH of from approx 5 to 9 and slowly adding vinyl oxirane at a temperature of from 20° to 80° C., the molar ratio of sulfinic acid II to vinyl oxirane being, for example, from 1:1.1 to 1:2.

Those phenylsulfones of formula I in which, with $R^2$ in the ortho-position relative to the group $SO_2$—X, $R^2$ and X together form the radical

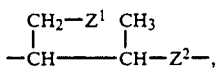

may be prepared, for example, by heating a compound of formula IV

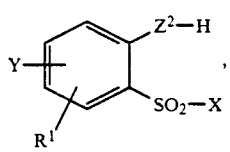

in which $R^1$, X, Y and $Z^2$ have the meanings stated above. This is preferably carried out in an inert organic solvent such as a $C_1$-$C_8$-alcohol, e.g. methanol, ethanol, propanol, isopropanol, butanol, isobutanol, pentanol, hexanol, heptanol, octanol or 2-ethylhexanol, an ether, e.g. tetrahydrofuran or dioxane, or an acetate, e.g. methyl or ethyl acetate, a temperature of from 40° to 120° C. being maintained.

If Y in formulae I, II and IV stands for nitro or $C_1$-$C_4$-alkanoylamino, it can be converted to the free amino group by known methods, for example by reduction of the nitro group or saponification of the alkanoylamino group.

Those compounds of formula I in which $Z^1$ denotes chlorine, $C_1$-$C_4$-alkanoyloxy, $C_1$-$C_4$-alkylsulfonyloxy, phenylsulfonyloxy, o- or p-tolylsulfonyloxy or sulfato may be obtained, for example, by reacting the corresponding hydroxy compounds ($Z^1$ =hydroxy) with a chlorinating reagent (such as thionyl chloride), a $C_1$-$C_4$-alkanoyl halide, a $C_1$-$C_4$-alkylsulfonic halide, a phenylsulfonic halide, an o- or p-tolylsulfonic halide or an acid anhydride, by methods known in the art.

The sulfinic acids of formula II, the compounds of formula IV and vinyl oxirane of formula III are known per se. The preparation of vinyl oxirane is described, for example, in Ber. Dt. Chem. Ges. Vol. 66, pp. 335 to 339, 1933.

The novel phenylsulfones of formula I are valuable intermediates for use in the synthesis of dyes. They may be used to advantage as reactive anchors or, alternatively, as diazo components (where Y=amino).

The invention is further illustrated by the following Examples.

EXAMPLE 1

A solution of 398 g of p-acetylaminobenzenesulfonic acid in 1000 ml of water was adjusted to pH 7.5 with sodium hydroxide solution. 190 g of vinyl oxirane were then added dropwise over a period of 3 hours at a temperature of from 40° to 45° C. Stirring was continued for a further 2 hours at 40°-45° C. The pH was continuously adjusted to 7.5 during the entire reaction by the dropwise addition of 10% w/w sulfuric acid. The precipitate obtained on cooling was isolated by filtration in vacuo and dried under reduced pressure at 50° C. There were obtained 392 g of the compound of the formula:

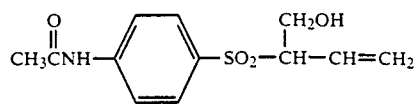

m.p. 117°–119° C.

H-NMR ($D_6$-DMSO):2.1 (intensity: grade 3), 3.7 (1), 3.9 (2), 5.0 (1; triplet=OH), 10.4 (1), 5.1 (1), 5.3 (1), 5.7 (1), 8.8 (4).

EXAMPLE 2

63.8 g of the compound obtained in Example 1 were heated in 250 g of 10% w/w hydrochloric acid for 4 hours at 100° C. The mixture was allowed to cool and its pH was adjusted to 9.5 to 10 with sodium hydroxide solution. It was then extracted twice with ethyl acetate. The organic phase was concentrated to give 46 g of an oil, which slowly crystallized. The resulting product had a melting point of 75°–80° C. and the following formula:

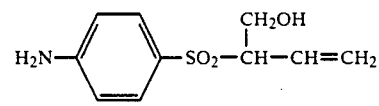

EXAMPLE 3

149.6 g of m-nitrobenzenesulfinic acid were dissolved in 650 ml of water at a pH of 7.5. 90 g of vinyl oxirane were added dropwise at a temperature of from 40° to 45° C. while the pH was kept at 7.5 by dropwise addition of 10% w/w sulfuric acid. On completion of the reaction, as may be determined by thin-layer chromatography, the mixture was extracted twice with 500 g of chloroform. The product obtained on concentration of the organic phase comprised 170 g of an oil, which slowly crystallized. This was recrystallized from n-butanol to give the compound of the following formula:

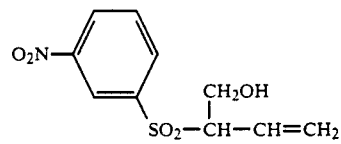

which melts at 45°–48° C.

H-NMR ($D_6$-DMSO): 3.9 (2), 4.3 (1), 5.2 (1; triplet- =OH), 5.3 (1), 5.4 (1), 5.8 (1) 8.0 (1), 8.3 (1), 8.6 (2).

EXAMPLE 4

25.7 g of the compound obtained in Example 3 were dissolved in 400 g of methanol and 2 g of propionic acid. 5 g of Raney nickel were added, and the mixture was hydrogenated at 40° C. under a pressure of 2 bar. On termination of hydrogen uptake, the catalyst was removed by filtration and the mother liquor was treated to remove the solvent. There remained 20.2 g of a yellow oil having the formula:

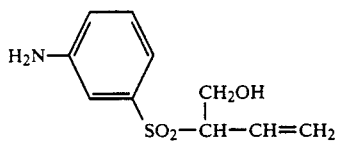

This product could be used without further purification for dye synthesis. Its structure was verified by NMR spectra.

EXAMPLE 5

85 g of 2-chloro-5-nitrobenzenesulfinic acid were dissolved in 400 ml of water at a pH of 7.5. Whilst maintaining a temperature of from 40° to 45° C., 56 g of vinyl oxirane were added dropwise over a period of 4 hours. At the same time, the pH was kept at 7.5 by additions of 10% w/w sulfuric acid. The mixture was cooled, extracted with ethyl acetate and concentrated to give 45 g of a yellow oil having the following formula:

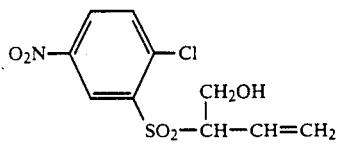

H-NMR (D$_6$-DMSO): 3.9 (2), 4.4 (1), 5.2 (1; triplet=OH), 5.3 (1), 5.4 (1), 5.8 (1), 8.0 (1), 8.6 (1), 8.7 (1). Chlorine: calculated 12.2% - found 12.1%.

EXAMPLE 6

A solution of 50 g of the compound obtained in Example 5 and 15 g of ethanolamine in 150 g of isopropanol was heated at 60° C. 3 g of ethanolamine were added after 4 hours and again after 6 hours. The solvent was distilled off under reduced pressure. There remained 68 g of a yellow oil, which crystallized on heating with n-butanol. The isolated and dried product melts at 212°–216° C. and NMR-spectroscopic analysis indicates the following formula:

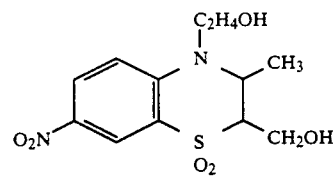

H-NMR (D$_6$-DMSO): 1.6 (3), 3.5 (2+1), 3.7 (2), 3.9 (2), 4.5 (1), 5.0 (1; triplet=OH), 5.1 (1; triplet=OH), 7.1 (1), 8.2 (1), 8.4 (1).

EXAMPLE 7

25 g of the compound obtained in Example 6 were reduced in 1000 g of methanol in a manner similar to that described in Example 4. There were isolated 20 g of an oil having the following formula, as determined by NMR-spectroscopic analysis:

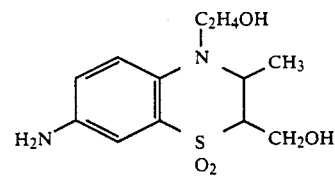

EXAMPLE 8

A solution of 58 g of the compound obtained in Example 5 and 30 g of N-methylethanolamine in 150 g of isopropanol was heated for 5 hours at a temperature of from 65° to 70° C. The solution was then poured into water, and the pH was adjusted to 1 with hydrochloric acid to cause separation of a yellow oil. Following extraction with ethyl acetate, the organic phase was dried over Na$_2$SO$_4$ and concentrated under reduced pressure. There were thus isolated 25 g of a yellow oil, to which the following formula can be ascribed as indicated by NMR-spectroscopic analysis.

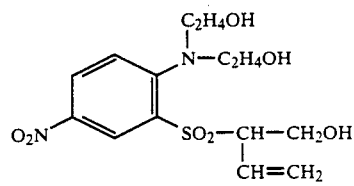

We claim:
1. A phenylsulfone of formula I

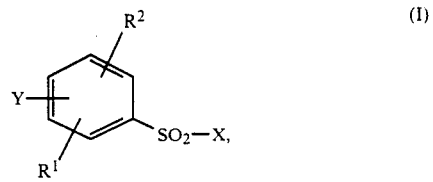

in which
R$^1$ is hydrogen, halogen, C$_1$–C$_4$-alkyl, nitro, hydroxysulfonyl, carboxyl, the radical —NR$^3$R$^4$,
  in which R$^3$ and R$^4$ are the same or different and denote hydrogen, C$_1$–C$_4$-alkyl or C$_2$–C$_4$-alkyl substituted by hydroxy, C$_1$–C$_4$-alkanoyloxy, C$_1$–C$_4$-alkoxy, hydroxysulfonyl, chlorine or bromine,
  or the radical S(O)$_n$R$^5$,
    in which n is 1 or 2 and R$^5$ denotes C$_1$–C$_4$-alkyl or C$_2$–C$_4$-alkyl substituted by hydroxy, chlorine, bromine, C$_1$–C$_4$-alkoxy, hydroxysulfonyl or sulfato,
with R$^2$ in the ortho-position relative to the group SO$_2$—X, R$^2$ and X together denote the radical

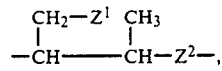

in which
Z$^1$ is hydroxy, chlorine, C$_1$–C$_4$-alkanoyloxy, C$_1$–C$_4$-alkylsulfonyloxy, phenysulfonyloxy, o- or p-tolylsulfonyloxy or sulfato and
Z$^2$ is imino or C$_1$–C$_4$-alkylimino optionally substituted by hydroxy, 2-hydroxyethylthio or 2-hydroxyethylsulfonyl, and
Y denotes amino, C$_1$–C$_4$-alkanoylamino or nitro.
2. A phenylsulfone as claimed in claim 1, wherein R$^2$ and X together denote the radical

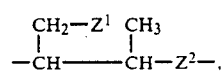

in which Z$^1$ has the meaning stated in claim 1 and Z$^2$ stands for C$_1$–C$_4$-alkylimino optionally substituted by hydroxy.

* * * * *